United States Patent
Smith (10) Patent No.: US 9,791,508 B2
(45) Date of Patent: Oct. 17, 2017

(54) DETECTING AND DISPLAYING FLAWS IN A DEVICE UNDER TEST

(71) Applicant: Nathan R. Smith, St. Charles, MO (US)

(72) Inventor: Nathan R. Smith, St. Charles, MO (US)

(73) Assignee: The Boeing Company, Chicago, IL (US)

( * ) Notice: Subject to any disclaimer, the term of this patent is extended or adjusted under 35 U.S.C. 154(b) by 87 days.

(21) Appl. No.: 15/002,162

(22) Filed: Jan. 20, 2016

(65) Prior Publication Data

US 2017/0205460 A1    Jul. 20, 2017

(51) Int. Cl.
*G01R 31/28*      (2006.01)
*G01R 31/3177*      (2006.01)
*G01R 31/317*      (2006.01)

(52) U.S. Cl.
CPC ... *G01R 31/3177* (2013.01); *G01R 31/31703* (2013.01); *G01R 31/31723* (2013.01)

(58) Field of Classification Search
CPC .......... G01R 31/3177; G01R 31/31703; G01R 31/31723
See application file for complete search history.

(56) References Cited

U.S. PATENT DOCUMENTS

| | | | | |
|---|---|---|---|---|
| 4,641,086 A | * | 2/1987 | Barr, IV | G01R 23/16 324/76.12 |
| 5,731,984 A | * | 3/1998 | Ullmann | G01R 31/31912 702/108 |
| 5,825,191 A | * | 10/1998 | Niijima | G01R 31/307 324/754.22 |
| 6,089,095 A | * | 7/2000 | Yang | G01N 29/0609 73/600 |
| 6,636,817 B2 | * | 10/2003 | Fioravanti | G11B 20/1816 360/25 |
| 6,981,417 B1 | | 1/2006 | Oravecz | |
| 6,986,091 B2 | * | 1/2006 | Moore | G01R 31/31709 713/500 |
| 7,079,971 B2 | * | 7/2006 | Fukuda | G11C 29/56 324/537 |

(Continued)

FOREIGN PATENT DOCUMENTS

CN      103018331 A      4/2013

OTHER PUBLICATIONS

Epoch 650 Ultrasonic Flaw Detector Getting Started Guide; Olympus Scientific Solutions Americas Corp., www.olympus-ims.com; Feb. 2015, (12 pages).

(Continued)

*Primary Examiner* — Esaw Abraham
(74) *Attorney, Agent, or Firm* — Toler Law Group, PC (57) ABSTRACT

An apparatus includes a receiver configured to receive signals based on an application of test signals to a device under test (DUT). The apparatus further includes a processor and a memory storing computer-executable instructions, that when executed by the processor, cause the processor to generate multiple display frames based on a frequency domain analysis of the received signals. Each display frame of the multiple display frames corresponds to a frequency band of the received signals.

17 Claims, 8 Drawing Sheets

(56) References Cited

U.S. PATENT DOCUMENTS

| | | | | |
|---|---|---|---|---|
| 7,080,292 B2* | 7/2006 | Moore | ............ | G01R 31/31709 |
| | | | | 714/700 |
| 8,837,294 B2* | 9/2014 | Frishberg | .............. | H04L 43/045 |
| | | | | 370/241 |
| 8,904,247 B2* | 12/2014 | Toyoda | ................... | H04L 43/50 |
| | | | | 714/715 |
| 8,914,246 B2* | 12/2014 | Chaji | ..................... | G09G 3/006 |
| | | | | 702/58 |

OTHER PUBLICATIONS

Epoch 650 Versatile and Rugged Flaw Detector; Olympus Scientific Solutions Americas Corp., www.olympus-ims.com; 2015 (8 pages).
Conventional UT and Phased Array Flaw Detector—OmniScan MXU-M—Manual Inspection Solution; Olympus NDT Inc., www.olympus-ims.com; 2010, (4 pages).
OmniScan MX with ECA/ECT Modules—Discover Eddy Current Color Imaging; Olympus NDT Inc., www.olympus-ims.com; 2013, (12 pages).
Office Action, European Application No. EP 17152491, mailed May 19, 2017, 8 pages.

\* cited by examiner

DETECTING AND DISPLAYING FLAWS IN A DEVICE UNDER TEST

FIELD

The present disclosure generally relates to detecting flaws in a device.

BACKGROUND

Detection and/or identification of structural flaws in devices is an important aspect of designing and manufacturing products. Various methods may be used to test for such flaws in a device under test (DUT). In certain cases, one or more image representations of the DUT may be generated to enable a user or viewer to visually identify the flaws.

SUMMARY

In an embodiment, a method includes receiving signals based on an application of test signals to a device under test (DUT). The method also includes generating multiple display frames based on a frequency domain analysis of the received signals, where each display frame of the multiple display frames corresponds to a frequency band of the received signals.

In another embodiment, an apparatus includes a receiver configured to receive signals based on an application of test signals to a device under test (DUT). The apparatus further includes a processor and a memory storing computer-executable instructions, that when executed by the processor, cause the processor to generate multiple display frames based on a frequency domain analysis of the received signals. Each display frame of the multiple display frames corresponds to a frequency band of the received signals.

In another embodiment, computer readable storage device storing computer-executable instructions, that when executed by at least one processor, causes the at least one processor to perform operations. The operations may include receiving signals based on an application of test signals to a device under test (DUT). The operations may also include generating multiple display frames based on a frequency domain analysis of the received signals, where each display frame of the multiple display frames corresponds to a frequency band of the received signals.

The described features, functions, and advantages may be achieved independently in various embodiments or may be combined in yet other embodiments further details of which can be seen with reference to the following description and drawings.

DETAILED DESCRIPTION

The present disclosure describes a system and method for detecting and displaying flaws in a device under test (DUT). According to a particular embodiment, a system may include a testing device and a DUT. The testing device may be coupled to a probe, and the probe may be move relative to one or more surfaces of the DUT to detect the presence of structural flaws or other physical features of the DUT. For example, the probe may include a first probe tip and a second probe tip, and each of the probe tips may contact a particular surface of the DUT. Further, the first probe tip may be configured to generate and apply a test signal to the particular surface of the DUT. In certain implementations, the test signal may be ultrasound signals and/or other electromagnetic signals. Additionally, the test signal may correspond to a sine wave that continuously changes in frequency (e.g., from approximately 25 Hertz (Hz) to 3 kHz).

The test signal, or one or more portions thereof, may be affected by a flaw or other physical features within the DUT, causing a signal (e.g., a reflected signal, a return signal, a through-transmission signal, resonant signal, and/or the like) to be generated. It will be appreciated that a flaw may be any physical feature in the DUT that is associated with a deformity and/or change in a material structure of the DUT. The second probe tip of the probe may be configured to receive the signal. In other embodiments, the test device may include different types of probe configurations in order to generate and receive signals. For example, the testing device may include a testing probe and a receiving probe, which both contact the particular surface of the DUT. The testing probe may be configured to generate the test signal and the receiving probe may be configured receive a signal based on the test signal. As another example, the testing device may include a probe having a probe element that is configured to both generate the test signal and receive a signal based on the test signal. In yet other implementations, the testing device may include a probe configuration to generate the test signal and receive a signal based on the testing signal without contacting the particular surface of the DUT.

One or more properties of the received signal may be analyzed by the testing device, such as amplitude, phase, and/or frequency of the received signal. Based on the one or more properties of the received signal, the testing device may be configured to perform a frequency domain analysis. In a particular embodiment, the frequency domain analysis may include determining one or more frequency responses based on received signals from different portions of the DUT. Further, frequency responses based on received signals from unflawed portions of the DUT may remain substantially consistent. For example, a first frequency response based on a first received signal from a first unflawed portion of the DUT may be the same or approximately the same as a second frequency response based on a second received signal from a second unflawed portion of the DUT.

In contrast, the frequency response based on a received signal from a portion of the DUT that includes a flaw may be substantially different from the frequency response based on a received signal from another portion of the DUT that does not include a flaw. For instance, a third frequency response based on a third received signal from a first flawed portion of the DUT may be substantially different from the first frequency response based on the first received signal from the first unflawed portion of the DUT. Moreover, different flaws in the DUT may be associated with different frequency responses of corresponding received signals. For example, the third frequency response based on the third received signal may be different from a fourth frequency response based on a fourth received signal from a second flawed portion of the DUT.

According to a particular embodiment, test data corresponding to frequency responses based on one or more of the received signals (e.g., reflected from multiple portions and/or physical features of the DUT) may be stored by the testing device. For instance, the test data may be stored in a memory or another storage device included in the testing device or an external computing device. The testing device may be configured to generate one or more images based on the stored test data. For example, the testing device may generate one or more C-scans based on the stored test data. A C-scan may be a planar image of the DUT that depicts the frequency response of one or more portions of the DUT relative to a particular frequency range (e.g., a frequency gate) based on the test signal(s). In some implementations, different frequency responses based on received signals from different portions of the DUT relative to the frequency gate may be represented using different colors in the C-scan image. For example, since unflawed portions of the DUT may be associated with relatively consistent frequency response relative to any frequency gate, the C-scan image may depict the unflawed portions with a first color. Further, as explained above, a flawed portion of the DUT may be associated with a different frequency response than an unflawed portion of the DUT. As such, the C-scan image may depict the flawed portion with one or more different colors than the unflawed portion.

A particular image (e.g., a particular C-scan image) may depict frequency responses associated with different portions of the DUT relative to a particular frequency gate. As such, a different image of the DUT (e.g., a different C-scan image) may be generated for each corresponding frequency gate. Viewing of multiple C-scan images may involve certain inefficiencies since there may be one or more time delays between the generation of each of the C-scan images. In a particular embodiment, the testing device, or an external computer associated with the testing device may be configured to generate multiple display frames. Each of the display frames may correspond to a different C-scan image. The display frames may be displayed sequentially, such as in a video, slide show, and/or other type of display format, which may enable a user to more quickly detect flaws in the DUT, and properties of the flaws (e.g., size and/or location).

Figure 1:
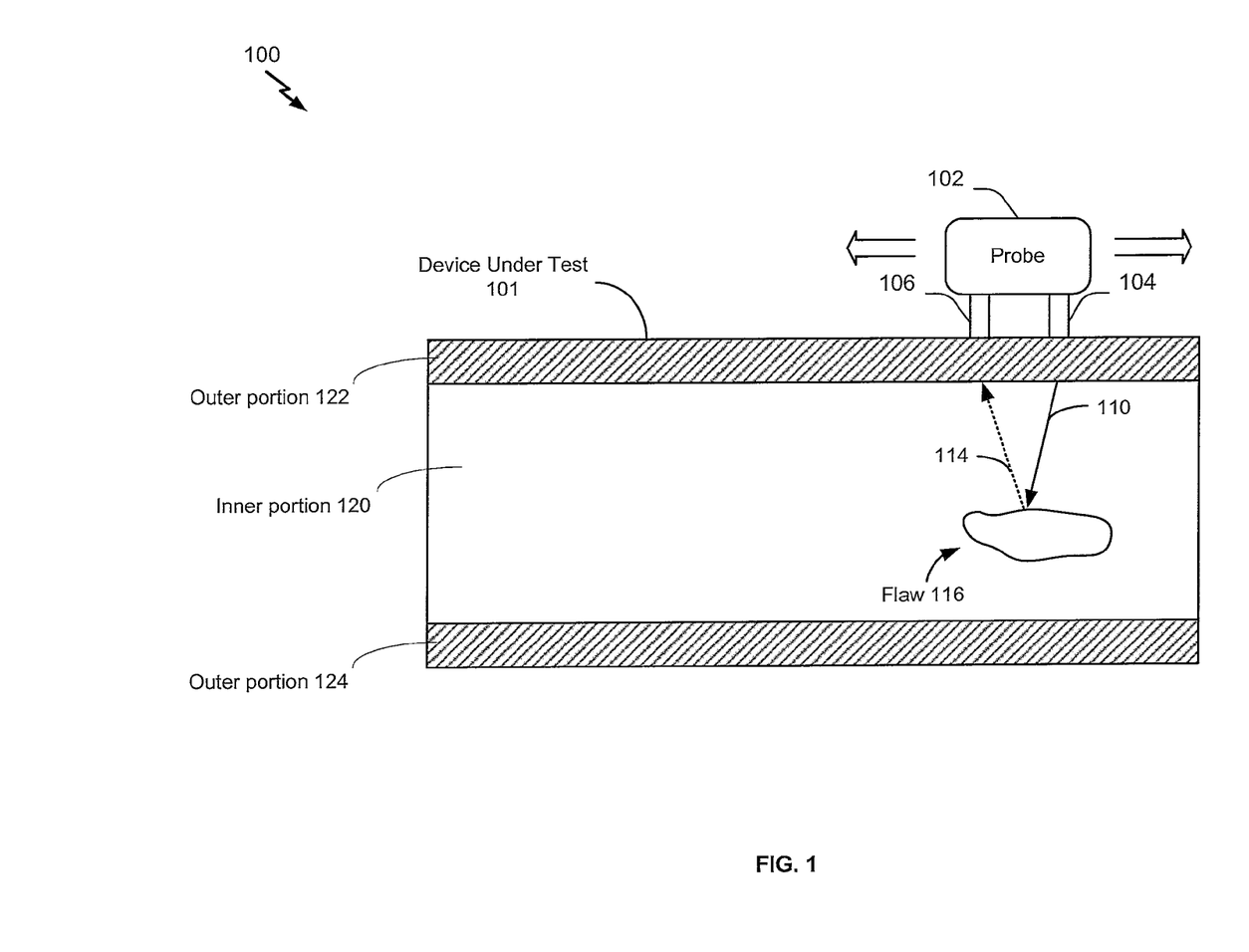
FIG. 1 is a block diagram of a particular embodiment of a system for detecting and displaying flaws in a device under test (DUT)

Referring to FIG. 1, a particular embodiment of a system for displaying flaws in a device under test (DUT) is illustrated and generally designated 100. The system 100 includes a DUT 101. The DUT 101 may include an inner portion 120 and one or more outer portions 122, 124. According to a particular embodiment, the inner portion 120 may be composed of a honeycomb-like material (e.g., a Nomex® honeycomb), and the outer portions 122, 124 may be composed of pre-cured laminate material. In other embodiments, the DUT 101 may include other materials, such as composite materials, metals, ceramics, polymers, etc.

A probe 102 may be used to detect the presence of one or more flaws in the DUT 101, such as flaw 116 in the inner portion 120 of the DUT 101. The flaw 116 may include any physical feature in the DUT 101 that is associated with a change in a material structure of the DUT 101. The probe 102 may be coupled to a testing device, as described in further detail with reference to FIG. 2. The probe 102 may include one or more probe tips, such as a transmitting probe tip 104 and a receiving probe tip 106. During operation, the probe 102 may be passed over one or more surfaces of the DUT 101, such as the outer portion 122 of the DUT 101. As the probe 102 is moved over the outer portion 122, the transmitting probe tip 104 may transmit one or more test signals, such as electromagnetic or acoustic waveforms (e.g., ultrasound, terahertz, microwave, and/or the like). The test signals, or one or more portions thereof, may reflect off one or more portions of the DUT 101, such as one or more physical features of the inner portion 120. As such, the receiving probe tip 106 may be configured to receive one or more received signals corresponding to the reflections of the test signals.

According to a particular embodiment, the test signals may include test signal 110. The test signal 110 may include an ultrasound signal, or another type of waveform that is capable of propagating through at least a portion of the DUT 101. The test signal 110 may correspond to a sine wave that continuously changes in frequency (e.g., from 25 Hz to 3 kHz). When the test signal 110 encounters a discontinuity or a portion of the DUT 101 that has different propagation characteristics for the test signal 110 (such as a flaw 116 or any other physical feature), at least a portion of the test signal 110 may be reflected and received as a received signal 114. The receiving probe tip 106 may be configured to receive the received signal 114. In other embodiments, the received signal 114 may correspond to other types of signals that may be generated as a result of applying the test signal 110 to the DUT 101. Although FIG. 1 illustrates a single test signal 110 and a single received signal 114, during use, multiple test signals may be transmitted by the transmitting probe tip 104, and multiple received signals may be received by the receiving probe tip 106 with respect to the flaw 116. Further, although not specifically illustrated in FIG. 1, characteristics of the received signal, such as an amplitude of the received signal 114 in a particular frequency band, may be related to characteristics of the flaw 116. Thus, by performing a frequency domain analysis of the received signals, multiple display frames (each corresponding to a frequency band of the received signals) can be generated to provide detailed information about the flaw 116 and other features of the DUT 101, as explained further below.

Figure 2:
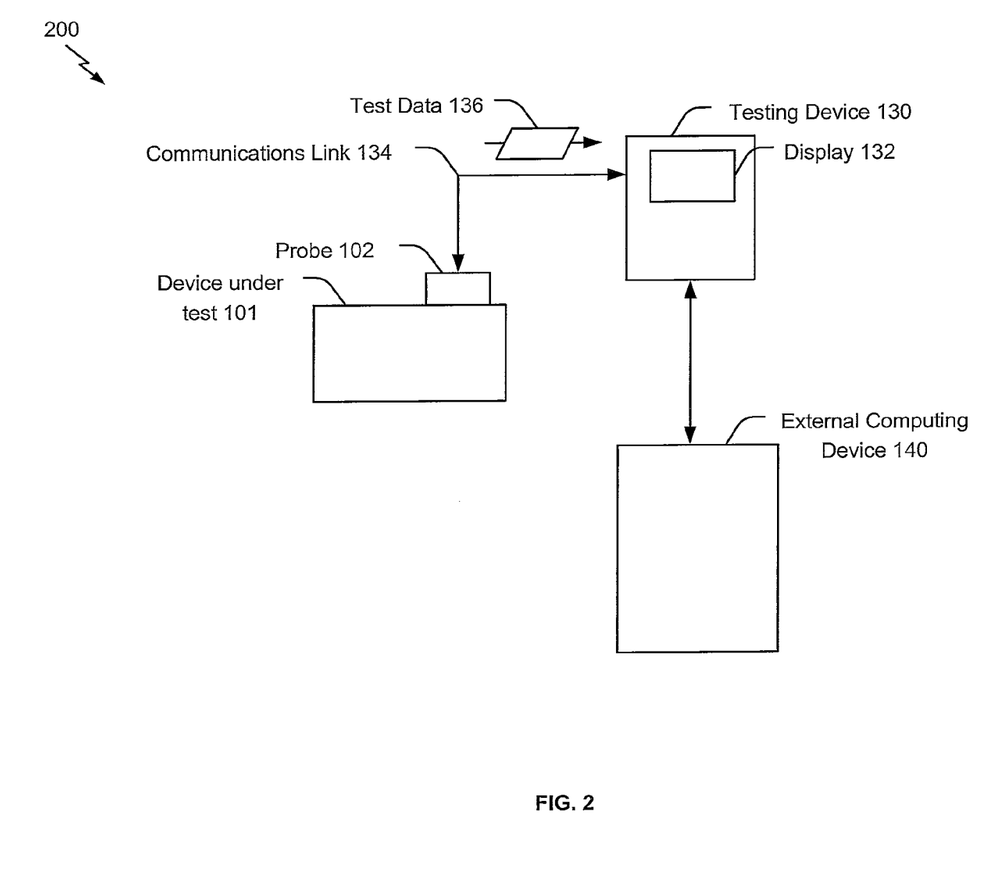
FIG. 2 is block diagram depicting another particular embodiment of a system for detecting and displaying flaws in a DUT.

FIG. 2 illustrates an example of a system 200 for displaying flaws, such as the flaw 116 of FIG. 1, in the DUT 101. FIG. 2 illustrates a testing device 130 that is coupled to the probe 102 via a communications link 134. The communications link 134 may be a wired and/or a wireless communications link that facilitates communication between the probe 102 and the testing device 130. The testing device 130 may include or be coupled to a display 132. Further, the testing device 130 may be coupled to an external computing device 140. Additionally, the testing device 130 may be a pitch-catch bond tester, a pulse-echo ultrasound tester, a through-transmission ultrasound tester, and/or any other type of non-destructive testing device.

The testing device 130 may be configured to drive the transmitting probe tip 104 of the probe 102, via the communications link 134, to generate one or more test signals (e.g., test signal 110). For example, the testing device 130 may send a signal (e.g., an analog signal or a digital signal) to the probe 102 to cause the transmitting probe tip 104 to generate the test signals and to apply the test signals to the DUT 101. Further, the probe 102 may send test data 136 via the communication link 134 to the testing device 130. The testing data 136 may include information descriptive of one or more properties of received signals (e.g., the received signal 114) received at the receiving probe tip 106 of the probe 102. Additionally, in some embodiments, the test data 136 may include information descriptive of movement or positions of the probe 102 with respect to the DUT 101. The test data 136 may include analog signals or digital signals.

According to a particular embodiment, the testing device 130 may be configured to perform a frequency domain analysis on the received signals based on the test data 136. In certain embodiments, performing the frequency domain analysis may include performing Fast Fourier Transforms with respect to the test data 136. For example, the testing device 130 may determine the frequency responses of multiple portions of the DUT 101 based on one or more received signals from the multiple portions. Frequency responses based on received signals from unflawed portions (or uniform portions) of the DUT 101 may be substantially consistent over time and through multiple frequency bands. For example, frequency responses based on received signals from the inner portion 120 of the DUT 101 that do not include the flaw 116 may be approximately the same.

In contrast, the frequency responses based on received signals from the flaw 116 (e.g., received signal 114) may be substantially different from the frequency responses based on received signals from unflawed (or uniform) portions of the DUT 101. In particular, relative to a particular frequency band, the frequency response based on a received signal from an unflawed portion of the DUT 101 may be relatively low (e.g., may have a small amplitude) as compared to the frequency response based on received signals (e.g., received signal 114) from the flaw 116.

The test data 136 may be stored in a memory or another storage device accessible to the testing device 130. In some implementations, the test data 136 may also be stored at the external computing device 140. Furthermore, the testing device 130 may be configured to generate, based on the test data 136, one or more images where each image corresponds to different frequency bands of the received signals received by the receiving probe tip 106 of the probe 102.

For example, the testing device 130 may generate one or more C-scans based on the test data 136. A C-scan may be a planar image (e.g., a view into or through the inner portion 120 from a surface corresponding to the outer portion 122 toward a surface or surfaces corresponding to the outer portion 124 of FIG. 1) of the DUT 101. Thus, each of the one or more C-scans represents the frequency response of one or more portions of the DUT 101 (e.g., different locations in the inner portion 120, including the flaw 116) relative to a particular frequency gate (e.g., a frequency band) based on various test signals (e.g., test signal 110). For instance, a first C-scan image may depict the frequency response of multiple portions of the DUT 101 relative to a first frequency gate (e.g., a first frequency band), and a second C-scan image may depict the frequency response of the multiple portions of the DUT 101 relative to a second frequency gate (e.g., a second frequency band). Further, a particular C-scan image may depict a particular portion of the DUT 101 in a particular color based on the frequency response of a received signal from the particular portion of the DUT 101. As such, different portions of the DUT 101 may be depicted in the particular C-scan image with different colors depending on the respective frequency responses of the corresponding received signals from those different portions. For example, since unflawed (or uniform) portions of the DUT 101 may be associated with relatively consistent frequency responses relative to any frequency gate, the particular C-scan image may depict the unflawed portions with a first color (e.g., a background or base color). Further, as explained above, the flaw 116 may be associated with a different frequency response than an unflawed portion of the DUT 101. As such, the C-scan image may depict the flaw 116 with one or more different colors than the unflawed (or uniform) portion.

As explained above, the particular image C-scan image may depict frequency responses associated with different portions of the DUT 101 relative to a particular frequency band and/or frequency gate. As such, a different image of the DUT (e.g., a different C-scan image) may be generated for each corresponding frequency gate. According to a particular embodiment, the testing device 130 may be configured to generate multiple C-scan images of the DUT 101 using multiple frequency gates. For instance, the testing device 130 may generate a first C-scan image corresponding to a first frequency gate, and subsequent C-scan images may correspond to other frequency gates that are based on increments from the first frequency gate. For example, the first frequency gate may correspond to a frequency band of 1 kHz-2 kHz. A second frequency gate may correspond to a second frequency band of 2 kHz-3 kHz, a third frequency gate may correspond to a third frequency band of 3 kHz-4 kHz, and so forth. The testing device 130 may be configured to generate any number of C-scan images corresponding to any number of frequency gates and/or frequency bands.

Further, the testing device 130 may be configured to generate respective display frames corresponding to each of the generated C-scan images. The testing device 130 may be configured to display the display frames (e.g., via the display 132). According to a particular embodiment, the testing device 130 may display the display frames sequentially, such as in a video format, slide show format, and/or any other type of display format. The display frames may be displayed according to increasing magnitudes of the frequency gates or another order.

Figure 3A:
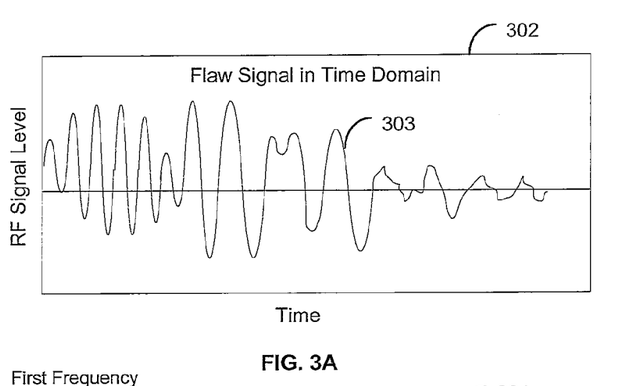
FIG. 3A is an illustration depicting a diagram of a received signal from a flaw in a DUT in the tune domain.

FIG. 3A illustrates an example diagram 302 of received signals 303 from the DUT 101. According to a particular embodiment, the received signals 303 may include the received signal 114 illustrated in FIG. 1. The diagram 302 depicts the received signals 303 as a function of time (e.g. in a time domain).

Figure 3B:
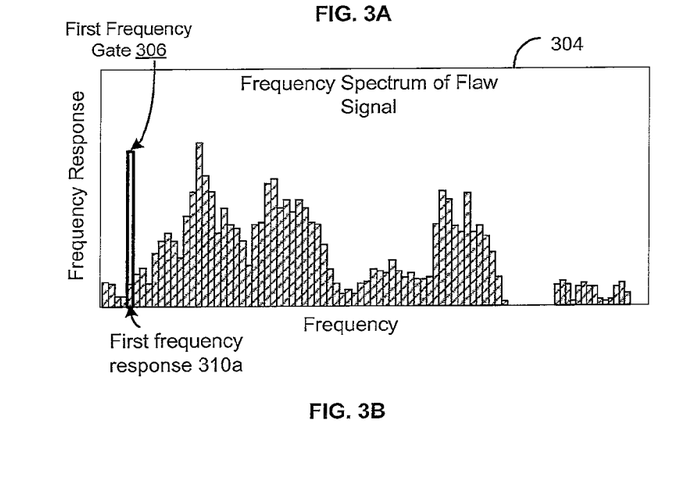
FIG. 3B is an illustration depicting a diagram of a frequency analysis of a received signal from a flaw in a DUT.

FIG. 3B illustrates an example frequency diagram 304 of the received signals 303 in a frequency domain. The frequency diagram 304 also depicts a first frequency gate 306 that may be used to generate a corresponding C-scan image. The first frequency gate 306 may be associated with a first frequency response 310a of the received signal 114 relative to the frequency band (e.g., 4 kHz-5 kHz) included in the first frequency gate 306.

Figure 3C:
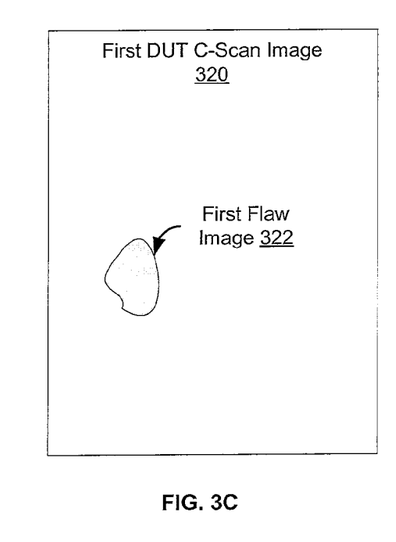
FIG. 3C is an illustration depicting a C-scan image corresponding to the frequency analysis of the received signal in FIG. 3B.

FIG. 3C illustrates a first C-scan image 320 based on the first frequency response 310a of the received signals 303 relative to the first frequency gate 306. As shown in FIG. 3C, the unflawed portions of the DUT 101 are represented in the first C-scan image 320 using a first display characteristic (e.g., the color white). Further, the first C-scan image also includes a first flaw image 322, which may be represented using a different display characteristic (e.g., a different color) than the unflawed portions of the DUT 101. In a particular embodiment, the first flaw image 322 may represent the first frequency response 310a of the flaw 116 in the DUT relative to the first frequency gate 306.

Figure 4A:
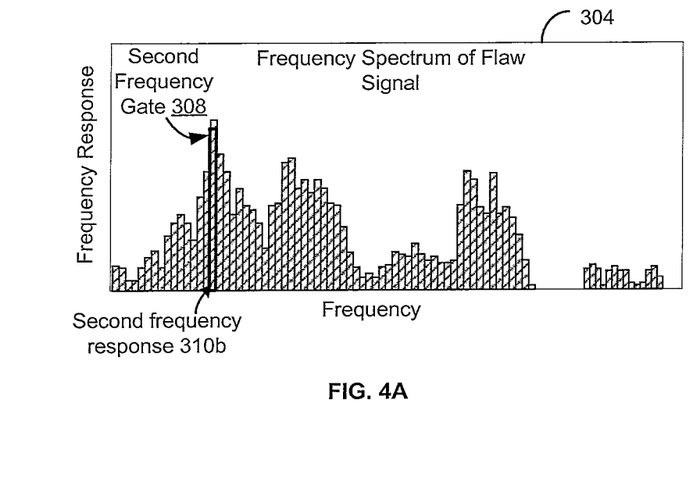
FIG. 4A is an illustration depicting a diagram of a frequency analysis of a received signal from a flaw in a DUT.

FIG. 4A illustrates the frequency diagram 304 of FIG. 3B with a second frequency gate 308. The second frequency gate 308 may be used to generate a second C-scan image of the DUT 101. Further, the second frequency gate 308 may be associated with a second frequency response 310b of the received signal 114 relative to a second frequency band (e.g., 9 kHz-10 kHz) of the second frequency gate 308.

Figure 4B:
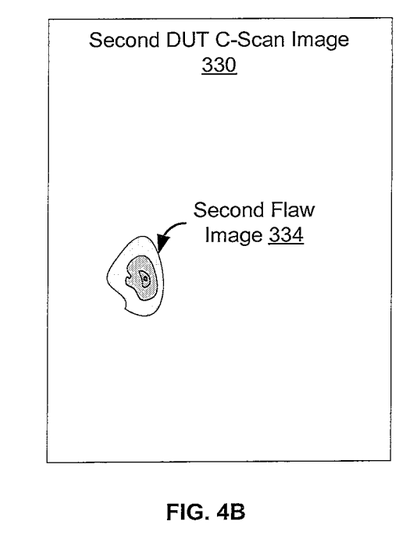
FIG. 4B is an illustration depicting a C-scan image corresponding to the frequency analysis of the received signal in FIG. 4B.

FIG. 4B illustrates a second C-scan image 330 based on the second frequency response 310b of the received signal 114 relative to the second frequency gate 308. As shown in FIG. 4B, the unflawed (or uniform) portions of the DUT 101 is represented in the second C-scan image 330 using the first color. Further, the second C-scan image 330 also includes a second flaw image 334. In a particular embodiment, the second flaw image 334 may represent the second frequency response 310b of the flaw 116 in the DUT relative to the second frequency gate 308. Since the magnitude of the second frequency response 310b is greater than the magnitude of the first frequency response 310a, the second flaw image 334 may be represented using different display characteristics (e.g. using a different color or using additional colors) compared with the first flaw image 322 in FIG. 3C. Thus, different C-scan images of the DUT 101 may depict the frequency responses associated with multiple portions of the DUT 101 relative to different frequency gates. Other display characteristics in addition to color may also be used to display differences in frequency response, such as particular drawing, markings, shadings, and/or the like.

Figure 5:
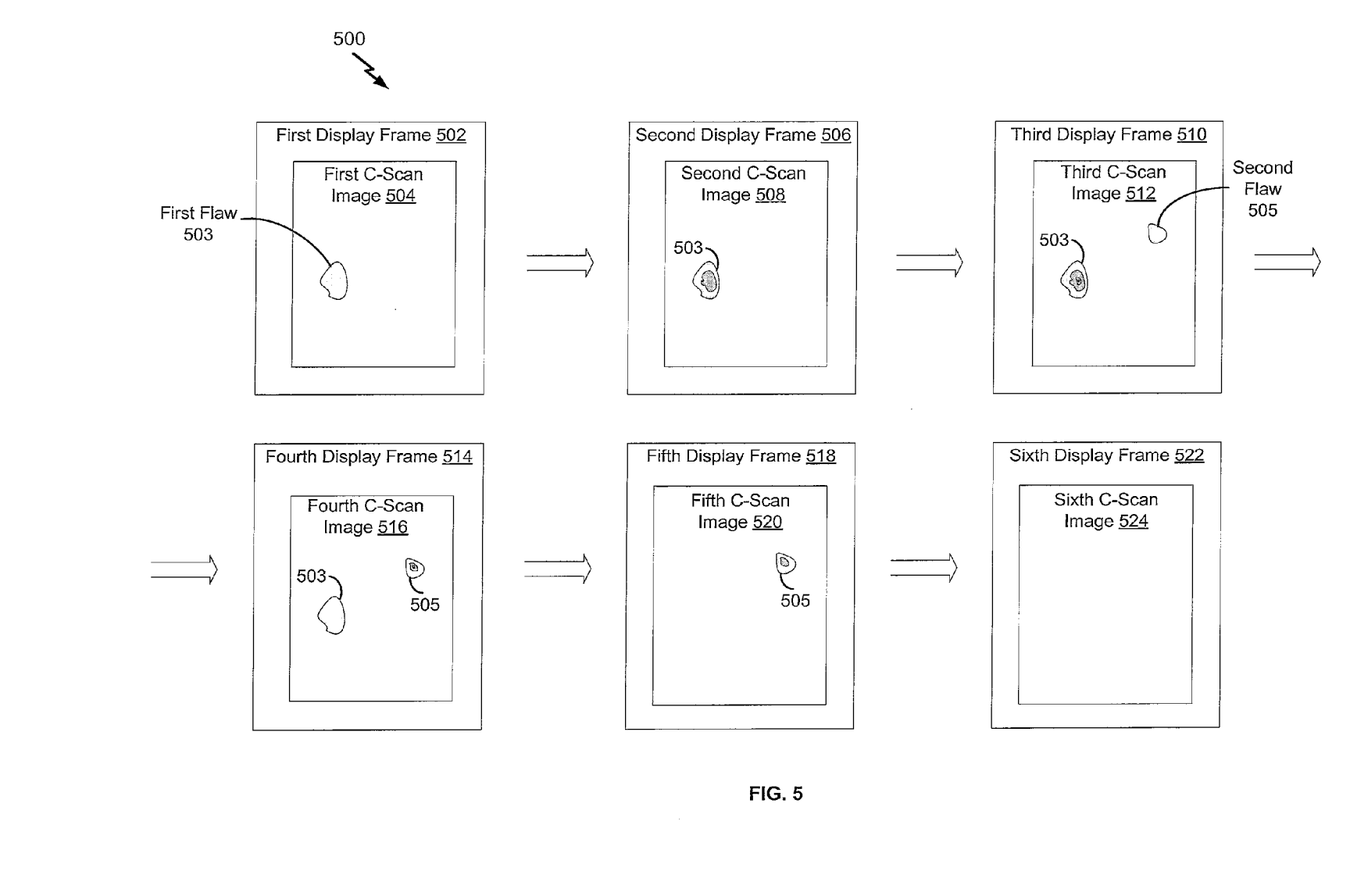
FIG. 5 depicts multiple display frames for detecting and displaying flaws in a DUT.

FIG. 5 illustrates a diagram 500 of multiple display frames depicting scans of a DUT according to a particular embodiment. For example, the multiple display frames may be generated by the testing device 130 or the external computing device 140 based on response signals received by the probe 102 from the DUT of FIGS. 1 and 2.

In the example illustrated in FIG. 5, the diagram 500 includes a first display frame 502, a second display frame 506, a third display frame 510, a fourth display frame 514, a fifth display frame 518, a sixth display frame 522. Other examples may include more of fewer display frames, depending, for example, on a number of frequency gates used. The first display frame 502 may correspond to a first C-scan image 504, the second display frame 506 may correspond to a second C-scan image 508, the third display frame 510 may correspond to a third C-scan image 512, the fourth display frame 514 may correspond to a fourth C-scan image 516, the fifth display frame 518 may correspond to a fifth C-scan image 520, and the sixth display frame 522 may correspond to a sixth C-scan image 524. Each of the C-scan images 504, 508, 512, 516, 520, and 524 may be associated with a respective frequency gate. Further, each of the C-scan images 504, 508, 512, 516, 520, and 524 may depict the frequency responses associated with different portions of a DUT (e.g., DUT 101) relative to the respective frequency gate. In FIG. 5, different cross-hatching or fill patterns in the C-scan images represent different display colors.

Differences in size, shape or display color of features in FIG. 5 indicate differences in frequency response at different frequency gates used to generate the display frames 502, 506, 510, 514, 518, 522. In particular, each pixel of a particular display frame may be associated with a display characteristic (e.g., a color), and the display characteristic may correspond to a magnitude (e.g., an amplitude) of a frequency domain analysis of one or more received signals with respect to a corresponding frequency gate. For example, the first C-scan image 504, the second C-scan image 508, the third C-scan image 512, and the fourth C-scan image 516 may include depictions of a first flaw 503. The frequency response of received signals from the first flaw 503 depicted in the third C-scan image 512 may be of a greater magnitude than the respective frequency responses of the received signals from the first flaw 503 in the first C-scan image 504, the second C-scan image 508, or the fourth C-scan image 516. As such, the third C-scan image 512 may depict the first flaw 503 with increased visibility (e.g., with more colors, different colors, higher opacity, or other display characteristics) compared to the depiction of the first flaw 503 in the first C-scan image 504, the second C-scan image 508, and the fourth C-scan image 516.

Further, the frequency response of received signals from the second flaw 505 depicted in the fourth C-scan image 516 may be of a greater magnitude than the respective frequency responses of the received signals from the second flaw 505 depicted in the third C-scan image 512 or the fifth C-scan image 520. As such, the fourth C-scan image 516 may depict the second flaw 505 with increased visibility (e.g., with more colors, different colors, higher opacity, or other display characteristics) compared to the depiction of the second flaw 505 in the third C-scan image 512 and the fifth C-scan image 520.

In the sixth C-scan image 524, the frequency responses based on received signals from the first flaw 503 and the second flaw 505 may be relatively low (e.g., similar to the frequency responses based on received signals from unflawed portions of the DUT). As such, neither the first flaw 503 nor the second flaw 505 may be visibly depicted in the sixth C-scan image 524.

According to a particular embodiment, the display frames 502, 506, 510, 514, 518, and 522 may be displayed sequentially. For example, a testing device, such as the testing device 130 illustrated in FIG. 2, may be configured to generate the display frames 502, 506, 510, 514, 518, and 522 and may be configured to sequentially display the display frames 502, 506, 510, 514, 518, and 522, such as in a video, slide show, and/or other display formats. In other implementations, an external computing device 140 may be used to display the display frames 502, 506, 510, 514, 518, and 522.

Thus, the display frames 502, 506, 510, 514, 518, and 522 generated by the testing device 130 may enable users to quickly and visually identify flaws and/or any other physical features in a DUT, such as DUT 101. For example, typical viewing of multiple C-scan images may involve selecting a frequency gate, generating a C-scan image corresponding to the selected gate, and displaying the C-scan image. In order to view a second C-scan image, a second frequency gate is selected, followed by generating a second C-scan image and then displaying the C-scan image. Typically, there may exist a relatively large time delay between displaying the C-scan image and displaying the second C-scan image, which may impair the user's viewing and visual identification of any flaws present in the DUT. The systems described in FIGS. 1-5 may eliminate such delays by collecting the test data 136, generating multiple images based on the test data, and displaying the images in a video format, slide show format, and/or other type of display format.

Figure 6:
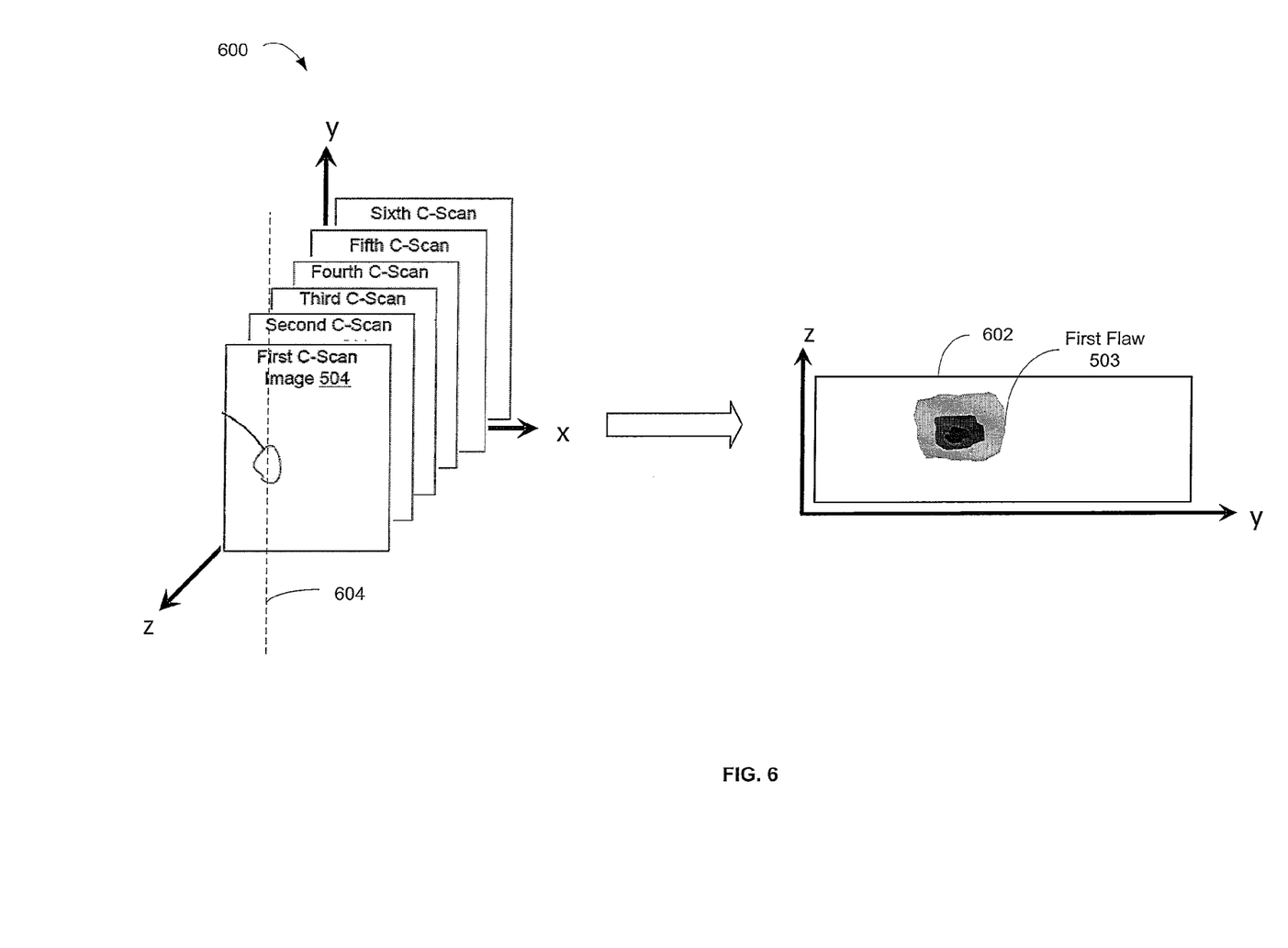
FIG. 6 depicts a cross-sectional scan image based on images included in the display frames of FIG. 5.

FIG. 6 illustrates a diagram 600 of a cross-sectional view of the scans depicted in FIG. 5 according to a particular embodiment. In certain embodiments, the cross-sectional view image 602 may be referred to as a B-scan, which may be based on the first C-scan image 504, the second C-scan image 508, the third C-scan image 512, the fourth C-scan image 516, the fifth C-scan image 520, and the sixth C-scan image 524. The cross-sectional scan image 602 may be a cross-sectional view of a group of the C-scan images 504, 508, 512, 516, 520 and 524.

For instance, the C-scan images 504, 508, 512, 516, 520 and 524 may be grouped together and aligned relative to an x-y-z coordinate space. The coordinate space may include an x-y plane corresponding to a surface of the DUT. The coordinate space may also include a z-axis corresponding to a frequency domain, and the group of the C-scan images 504, 508, 512, 516, 520 and 524 may be aligned along the z-axis (e.g., according to their corresponding frequency gates). A cross-sectional scan image 602 may be generated based on the group of the C-scan images 504, 508, 512, 516, 520 and 524. For example, the testing device 130 and/or the external computing device 140 may be configured to generate the cross-sectional scan image 602.

The cross-sectional scan image 602 may depict a cross section of the grouped C-scan images 504, 508, 512, 516, 520 and 524. The cross section may be generated along a line indicated by cross-sectional axis 604. According to a particular embodiment, the cross-sectional scan image 602 may depict a cross-section of the grouped C-scan images 504, 508, 512, 516, 520 and 524 relative to a y-z plane in the coordinate space. It will be appreciated that other cross-sectional scan images may be generated using different cross-sectional axes and different planes with respect to the coordinate space and the group of C-scan images 504, 508, 512, 516, 520 and 524.

Further, the cross-sectional scan image 602 may be included in one or more display frames for display, such as by the testing device 130 and/or the external computing device 140. In other embodiments, multiple cross-sectional scan images associated with different cross-sectional axes may be generated with respect to the group of the C-scan images 504, 508, 512, 516, 520 and 524. As such, each of the cross-sectional scan images may be displayed in a different display frame, which may be displayed in a video format, slide show format, and/or other type of display format.

Figure 7:
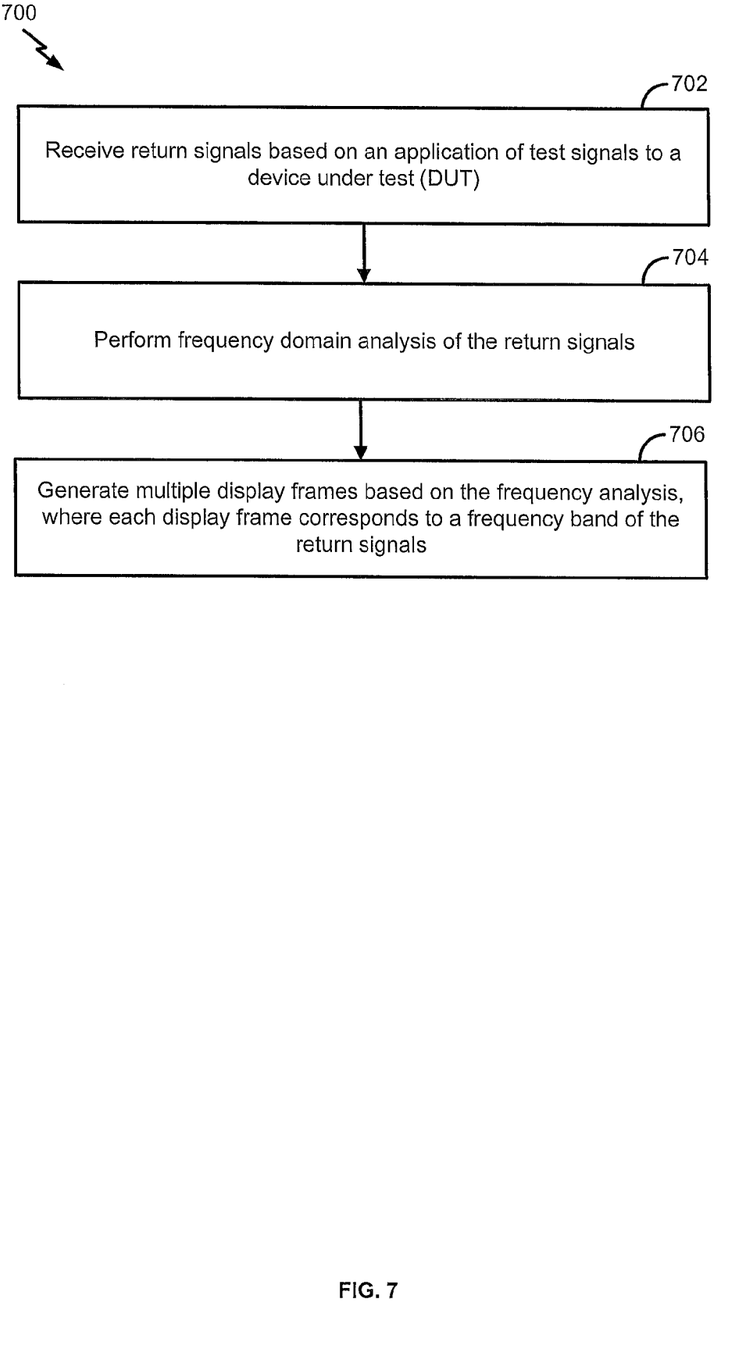
FIG. 7 is a flowchart depicting an exemplary embodiment of a method of detecting and displaying flaws in a DUT.

FIG. 7 is a flowchart depicting an exemplary embodiment of a method 700 for displaying and detecting flaws in a DUT. The method 700 may be performed by a testing device 130, an external computing device 140, or a combination thereof.

At 702, the method 700 may include receiving received signals based on an application of test signal to a DUT. For example, the testing device 130 of FIG. 2 may receive the test data 136 which may include or be determined based on the received signal 114 of FIG. 1. The received signal 114 may be based on an application of the test signal 110 of FIG. 1 by the probe 102.

At 704, the method 700 may include performing frequency domain analysis of the received signals. For instance, the testing device 130 and/or the external computing device 140 may be configured to determine one or more frequency responses based on the received signals from different portions of the DUT 101. To illustrate, the received signals 303 of FIG. 3A may be transformed into a frequency domain. In the frequency domain, a magnitude of the response signal in each of several frequency bands (e.g., the first frequency gate 306 of FIG. 3B and the second frequency gate 308 of FIG. 4A) may be determined.

At 706, the method 700 may include generating multiple display frames based on the frequency analysis, where each display frame corresponds to a frequency band of the received signals. For example, the testing device 130 and/or the external computing device 140 may be configured to generate multiple display frames, such as the multiple display frames 502, 506, 510, 514, 518, and 522 of FIG. 5. Each of the display frames may correspond to respective C-scan images, and each of the C-scan images may correspond to respective frequency gates and/or frequency bands. In each of the multiple display frames, a display characteristic (e.g. a color, an opacity, an intensity) associated with a particular pixel may be selected based on an amplitude of a frequency domain analysis of the received signal in a particular frequency band. In a particular embodiment, as described with reference to FIG. 5, the multiple display frames may be presented sequentially in a video.

Figure 8:
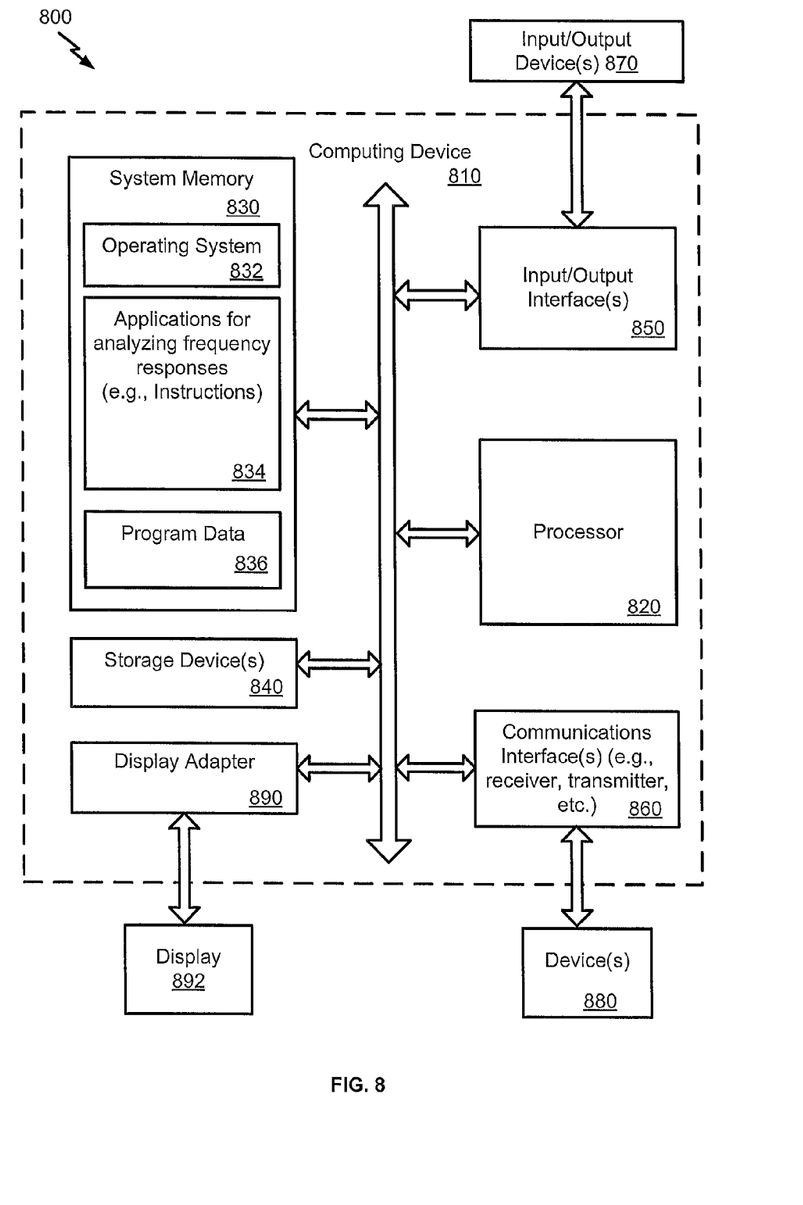
FIG. 8 is an illustration of a block diagram of a computing environment including a general purpose computing device configured to support embodiments of computer-implemented methods and computer-executable program instructions (or code) according to the present disclosure.

FIG. 8 is an illustration of a block diagram of a computing environment 800 including a general purpose computing device 810 configured to support embodiments of computer-implemented methods and computer-executable program instructions (or code) according to the present disclosure. For example, the computing device 810, or portions thereof, may execute instructions to perform the functions of a testing device 130 and/or an external computing device 140. The instructions to control the testing device 130 and/or the external computing device 140 may include instructions to perform a frequency domain analysis on one or more received signals reflected from test signals applied to various portions of a device under test. The instructions to control the testing device 130 and/or the external computing device 140 may further include instructions to generate one or more display frames based on the frequency analysis, wherein each display frame corresponds to a frequency band of the received signals. The computing device 810, or portions thereof, may further execute instructions according to any of the methods described herein.

The computing device 810 may include a processor 820. The processor 820 may communicate with the system memory 830, one or more storage devices 840, one or more input/output interfaces 850, one or more communications interfaces 860, or a combination thereof. The system memory 830 may include volatile memory devices (e.g., random access memory (RAM) devices), nonvolatile memory devices (e.g., read-only memory (ROM) devices, programmable read-only memory, and flash memory), or both. The system memory 830 may include an operating system 832, which may include a basic/input output system for booting the computing device 810 as well as a full operating system to enable the computing device 810 to interact with users, other programs, and other devices. The system memory 830 may include one or more applications 834 which may be executable by the processor 820. For example, the one or more applications 834 may include instructions executable by the processor 820 to control the testing device 130 and/or the external computing device 140. The system memory 830 may include program data 836 usable for controlling the testing device 130 and/or the external computing device 140.

The processor 820 may also communicate with one or more storage devices 840. For example, the one or more storage devices 840 may include nonvolatile storage devices, such as magnetic disks, optical disks, or flash memory devices. The storage devices 840 may include both removable and non-removable memory devices. The storage devices 840 may be configured to store an operating system, images of operating systems, applications, and program data. In a particular embodiment, the memory 830, the storage devices 840, or both, include tangible computer-readable media.

The processor 820 may also communicate with one or more input/output interfaces 850 that enable the computing device 810 to communicate with one or more input/output devices 870 to facilitate user interaction. The input/output interfaces 850 may include serial interfaces (e.g., universal serial bus (USB) interfaces or Institute of Electrical and Electronics Engineers (IEEE) 1394 interfaces), parallel interfaces, display adapters, audio adapters, and other interfaces. The input/output devices 870 may include keyboards, pointing devices, displays, speakers, microphones, touch screens, and other devices. The processor 820 may detect interaction events based on user input received via the input/output interfaces 850. Additionally, the processor 820 may send a display to a display device via the display adaptor 890 for display on a display 892.

The processor 820 may communicate with devices 880 via the one or more communications interfaces 860. The one or more communications interfaces 860 may include wired Ethernet interfaces, IEEE 802 wireless interfaces, other wireless communication interfaces, or other network interfaces. The devices 880 or controllers may include host computers, servers, workstations, and other computing devices.

Embodiments described above are illustrative and do not limit the disclosure. It is to be understood that numerous modifications and variations are possible in accordance with the principles of the present disclosure.

The illustrations of the embodiments described herein are intended to provide a general understanding of the structure of the various embodiments. The illustrations are not intended to serve as a complete description of all of the elements and features of apparatus and systems that utilize the structures or methods described herein. Many other embodiments may be apparent to those of skill in the art upon reviewing the disclosure. Other embodiments may be utilized and derived from the disclosure, such that structural and logical substitutions and changes may be made without departing from the scope of the disclosure. For example, method steps may be performed in a different order than is shown in the figures or one or more method steps may be omitted. Accordingly, the disclosure and the figures are to be regarded as illustrative rather than restrictive.

Moreover, although specific embodiments have been illustrated and described herein, it should be appreciated that any subsequent arrangement designed to achieve the same or similar results may be substituted for the specific embodiments shown. This disclosure is intended to cover any and all subsequent adaptations or variations of various embodiments. Combinations of the above embodiments, and other embodiments not specifically described herein, will be apparent to those of skill in the art upon reviewing the description.

The Abstract of the Disclosure is submitted with the understanding that it will not be used to interpret or limit the scope or meaning of the claims. In addition, in the foregoing Detailed Description, various features may be grouped together or described in a single embodiment for the purpose of streamlining the disclosure. This disclosure is not to be interpreted as reflecting an intention that the claimed embodiments require more features than are expressly recited in each claim. Rather, as the following claims reflect, the claimed subject matter may be directed to less than all of the features of any of the disclosed embodiments.

What is claimed is:

1. A method comprising:
   receiving signals based on an application of test signals to a device under test (DUT); and
   generating multiple display frames based on a frequency domain analysis of the received signals, each display frame of the multiple display frames corresponding to a frequency band of the received signals, wherein a particular display frame of the multiple display frames is associated with a particular frequency band and the particular display frame depicts a physical feature of the DUT based on the particular frequency band.

2. The method of claim 1, further comprising displaying the multiple display frames sequentially in a video.

3. The method of claim 1, wherein a display characteristic is associated with a pixel of the particular display frame, the display characteristic corresponding to an amplitude of a first frequency domain analysis of a first received signal.

4. The method of claim 1, wherein receiving the received signals comprises accessing reflected signals corresponding to one or more portions of the test signals reflected by physical features of the DUT.

5. The method of claim 1, wherein the particular display frame corresponds to a C-scan of the DUT based on the particular frequency band.

6. The method of claim 1, further comprising generating a cross-sectional scan image based on the multiple display frames, the cross-sectional scan image depicting a cross-section of a group of images corresponding to the multiple display frames.

7. The method of claim 1, wherein the test signals comprise at least one of ultrasound signals or electromagnetic signals.

8. An apparatus, comprising:
   a receiver configured to receive signals based on an application of test signals to a device under test (DUT);
   a processor; and
   a memory storing computer-executable instructions, that when executed by the processor, cause the processor to generate multiple display frames based on a frequency domain analysis of the received signals, each display frame of the multiple display frames corresponding to a frequency band of the received signals, wherein a particular display frame of the multiple display frames is associated with a particular frequency band and the particular display frame depicts a physical feature of the DUT based on the particular frequency band.

9. The apparatus of claim 8, wherein the computer-executable instructions further cause the processor to display the multiple display frames sequentially in a video.

10. The apparatus of claim 8, wherein a display characteristic is associated with a pixel of the particular display frame, the display characteristic corresponding to an amplitude of a first frequency domain analysis of a first received signal.

11. The apparatus of claim 8, wherein receiving the received signals comprises receiving reflected signals corresponding to one or more portions of the test signals reflected by physical features of the DUT.

12. The apparatus of claim 8, wherein the particular display frame corresponds to a C-scan of the DUT based on the particular frequency band.

13. The apparatus of claim 8, wherein the test signals comprise at least one of ultrasound signals or electromagnetic signals.

14. A computer readable storage device storing computer-executable instructions, that when executed by at least one processor, causes the at least one processor to perform operations comprising:
   receiving signals based on an application of test signals to a device under test (DUT); and
   generating multiple display frames based on a frequency domain analysis of the received signals, each display frame of the multiple display frames corresponding to a frequency band of the received signals, wherein a particular display frame of the multiple display frames is associated with a particular frequency band and the particular display frame depicts a physical feature of the DUT based on the particular frequency band.

15. The computer readable storage device of claim 14, wherein the operations further comprise displaying the multiple display frames sequentially in a video.

16. The computer readable storage device of claim 14, wherein a display characteristic is associated with a pixel of the particular display frame, the display characteristic corresponding to an amplitude of a first frequency domain analysis of a first received signal.

17. The computer readable storage device of claim 14, wherein receiving the received signals comprises receiving reflected signals corresponding to one or more portions of the test signals reflected by physical features of the DUT.

* * * * *